(12) United States Patent
Adams et al.

(10) Patent No.: US 8,298,519 B2
(45) Date of Patent: Oct. 30, 2012

(54) HAIR TREATMENT COMPOSITIONS INCORPORATING HAIR SUBSTANTIVE POLYMERS

(75) Inventors: Gerald Adams, Wirral (GB); Kelvin Brian Dickinson, Wirral (GB); Ezat Khoshdel, Wirral (GB); Neil Scott Shaw, Wirral (GB); Ximei Yao, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 763 days.

(21) Appl. No.: 12/438,977

(22) PCT Filed: Aug. 14, 2007

(86) PCT No.: PCT/EP2007/058412
§ 371 (c)(1),
(2), (4) Date: Feb. 26, 2009

(87) PCT Pub. No.: WO2008/025671
PCT Pub. Date: Mar. 6, 2008

(65) Prior Publication Data
US 2010/0015077 A1    Jan. 21, 2010

(30) Foreign Application Priority Data
Aug. 30, 2006   (GB) .................................. 0617024.5

(51) Int. Cl.
*A61K 8/72* (2006.01)
(52) U.S. Cl. .................................................. 424/70.11
(58) Field of Classification Search .................. 424/423; 514/12; 524/17
See application file for complete search history.

(56) References Cited

U.S. PATENT DOCUMENTS

| | | | | |
|---|---|---|---|---|
| 5,286,979 A * | 2/1994 | Berliner et al. | ............ | 250/515.1 |
| 5,627,148 A | 5/1997 | Dubief et al. | ................ | 510/122 |
| 6,150,146 A * | 11/2000 | Hamade et al. | ............... | 435/155 |
| 6,159,454 A * | 12/2000 | Schuhmacher et al. | ........ | 424/59 |
| 6,479,198 B2 * | 11/2002 | Makino et al. | .................. | 430/17 |
| 2002/0007521 A1 | 1/2002 | Lang et al. | ........................ | 8/405 |
| 2002/0046432 A1 | 4/2002 | Rondeau | .......................... | 8/407 |
| 2004/0244122 A1 | 12/2004 | DeLa Mettrie et al. | .......... | 8/401 |
| 2006/0009550 A1 * | 1/2006 | Messersmith et al. | .......... | 524/17 |

FOREIGN PATENT DOCUMENTS

WO  03/008376  1/2003

OTHER PUBLICATIONS

Cosmetics Design Europe, "Anti-ageing for the hair" (May 16, 2005) [Downloaded Sep. 23, 2011] [Retrieved from internet <URL: http://www.cosmeticdesign-europe.com/content/view/print/17511] (2 pages).*
Merck Index, Ethyl Acetate (Knovel database (Merck Sharp & Dohme Corp. 2006, 2012)).*
PCT International Search Report in a PCT application PCT/EP2007/058412.
GB Search Report in a GB application GB 0617024.5.

* cited by examiner

*Primary Examiner* — Tracy Vivlemore
*Assistant Examiner* — Miriam A Levin
(74) *Attorney, Agent, or Firm* — Ronald A. Koatz

(57) ABSTRACT

The invention provides a hair treatment composition comprising a hair substantive polymer, the hair substantive polymer comprising a polymeric backbone bearing: (a) at least one side chain which is formed from a hair fiber targeting group which is covalently linked to the polymeric backbone, the hair fiber targeting group being a non-cationic species which is capable of specifically interacting with the protein surface of the hair fiber in a non-covalent interaction having a bond energy ranging from 0.5 to 3 Kcal/mol, when the composition is applied to hair; (b) preferably, at least one side chain which is different to side chain (a) and which comprises a hair benefit agent. Compositions of the invention provide for deposition and delivery of benefit agents to hair in a more efficient and targeted manner.

8 Claims, No Drawings

HAIR TREATMENT COMPOSITIONS INCORPORATING HAIR SUBSTANTIVE POLYMERS

FIELD OF THE INVENTION

The invention relates to hair treatment compositions, which incorporate hair substantive polymers.

The compositions are particularly suitable for application to hair to deliver hair benefit agents to the hair fibre.

BACKGROUND AND PRIOR ART

A particular problem in the field of hair treatment is that of how to deliver benefit agents to the hair from "rinse-off" products like shampoos and conditioners, the problem simply being that a substantial proportion of the benefit agents may be washed away with the rinse water.

Benefit agents include such things as conditioning agents, perfumes, colorants, feel modifiers, lustrants, sun screens, nutrients, moisturisers, styling agents and medicinal agents (such as germicides, antidandruff and anti-pruritic agents).

Two methods are commonly used to enhance the deposition of benefit agents onto hair.

One method is to use large droplets of oil carrying a benefit agent in a shampoo or conditioner base. This method relies on physical contact between the hair and the droplets, followed by spreading of the oil droplets over the hair surface. This can, however, lead to the hair feeling greasy or heavy, and looking dull and lifeless because of the extensive spreading of the oil and its absorption by the hair.

Another method is to employ a deposition polymer, which is usually a cationic deposition polymer. Such systems rely solely on electrostatic attractive forces between oppositely charged species. This means in practice that other insoluble materials may be indiscriminately deposited onto the hair. This can lead to dulling of the hair, loss of shine and also to a heavy feel for some consumers.

There is a need for hair treatment compositions which provide for deposition and delivery of benefit agents to hair in a more efficient and targeted manner.

The present inventors have found that this problem can be solved by the use of certain hair substantive polymers which are able to interact specifically with the protein surface of the hair fibre.

SUMMARY OF THE INVENTION

In a first aspect of the present invention, there is provided a hair treatment composition comprising a hair substantive polymer, the hair substantive polymer comprising a polymeric backbone bearing:
  (a) at least one side chain which is formed from a hair fibre targeting group which is covalently linked to the polymeric backbone, the hair fibre targeting group being a non-cationic species which is capable of specifically interacting with the protein surface of the hair fibre in a non-covalent interaction having a bond energy ranging from 0.5 to 3 Kcal/mol, when the composition is applied to hair;
  (b) preferably, at least one side chain which is different to side chain (a) and which comprises a hair benefit agent.

The invention further provides a hair treatment composition comprising a cosmetically acceptable carrier material and a hair substantive polymer, the hair substantive polymer comprising a polymeric backbone bearing at least one side chain comprising a catechol group, said side chain being covalently linked to the polymeric backbone.

In a second aspect of the invention, there is provided a method of treating human hair comprising the application of a hair treatment composition according to the first aspect of the invention.

In a related aspect of the invention, there is provided a method of treating the human hair comprising the application of a hair substantive polymer, the hair substantive polymer comprising a polymeric backbone bearing at least one side chain comprising a catechol group, said side chain being covalently linked to the polymeric backbone.

DETAILED DESCRIPTION

Hair Substantive Polymer
Polymeric Backbone

The hair substantive polymer of the invention comprises a polymeric backbone.

The polymeric backbone may suitably be chosen from homo- and co-polymers; linear, branched, hyperbranched, dendritic and multi-arm star polymers; random and block polymers; and crosslinked polymers.

Any polymerizable monomers may be used to form the polymeric backbone, such as monomers which may be polymerized by radical, anionic, cationic, co-ordination or ring opening polymerisation processes.

Monomers useful in forming the polymeric backbone include ethylenically unsaturated polymerisable monomers.

By "polymerisable" is meant monomers that can be polymerised by reaction between the monomers to form an extended polymer chain.

By "ethylenically unsaturated" is meant monomers that contain at least one polymerisable carbon-carbon double bond (which can be mono-, di-, tri- or tetra-substituted). Either a single monomer or a combination of two or more monomers can be utilised. In either case, the monomers are selected to meet the physical and chemical requirements of the final polymer.

Representative non-limiting examples of monomers useful herein include protected or non-protected acrylic acid and methacrylic acid and salts, esters and amides thereof.

The salts can be derived from any of the common non-toxic metal, ammonium, or substituted ammonium counter ions.

The esters can be derived from $C_{1-40}$ straight chain, $C_{3-40}$ branched chain, or $C_{3-40}$ carbocyclic alcohols, from polyhydric alcohols having from about 2 to about 8 carbon atoms and from about 2 to about 8 hydroxyl groups (non-limiting examples of which include ethylene glycol, propylene glycol, butylene glycol, hexylene glycol, glycerol, and 1,2,6-hexanetriol); from amino alcohols (non-limiting examples of which include aminoethanol, dimethylaminoethanol and diethylaminoethanol and their quaternized derivatives); or from alcohol ethers (non-limiting examples of which include methoxyethanol and ethoxyethanol).

The amides can be unsubstituted, N-alkyl or N-alkylamino mono-substituted, or N,N-dialkyl, or N,N-dialkylamino disubstituted, wherein the alkyl or alkylamino groups can be derived from $C_{1-40}$ straight chain, $C_{3-40}$ branched chain, or $C_{3-40}$ carbocyclic moieties. In addition, the alkylamino groups can be quaternized.

Other useful monomers include: vinyl and allyl esters of $C_{1-40}$ straight chain, $C_{3-40}$ branched chain, or $C_{3-40}$ carbocyclic carboxylic acids; vinyl and allyl halides (e.g. vinyl chloride, allyl chloride); pyridines substituted with one or more vinyl or allyl groups (e.g. vinyl pyridine, allyl pyridine); vinylidene chloride; and hydrocarbons having at least one unsaturated carbon-carbon double bond (e.g. styrene, alpha-methylstyrene, t-butylstyrene, butadiene, isoprene, cyclohexadiene, ethylene, propylene, 1-butene, 2-butene, isobutylene, p-methylstyrene); and mixtures thereof.

Preferred monomers useful herein include those selected from protected and unprotected acrylic acid, methacrylic acid, ethacrylic acid, methyl acrylate, ethyl acrylate, n-butyl acrylate, iso-butyl acrylate, t-butyl acrylate, 2-ethylhexyl acrylate, decyl acrylate, octyl acrylate, methyl methacrylate, ethyl methacrylate, n-butyl methacrylate, iso-butyl methacrylate, t-butyl methacrylate, 2-ethylhexyl methacrylate, decyl methacrylate, methyl ethacrylate, ethyl ethacrylate, n-butyl ethacrylate, iso-butyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, 2-hydroxypropyl acrylate, hydroxypropyl methacrylate, glyceryl monoacrylate, glyceryl monoethacrylate, glycidyl methacrylate, glycidyl acrylate, acrylamide, methacrylamide, ethacrylamide, N-methyl acrylamide, N,N-dimethyl acrylamide, N,N-dimethyl methacrylamide, N-ethyl acrylamide, N-isopropyl acrylamide, N-butyl acrylamide, N-t-butyl acrylamide, N,N-di-n-butyl acrylamide, N,N-diethylacrylamide, N-octyl acrylamide, N-octadecyl acrylamide, N,N-diethylacrylamide, N-phenyl acrylamide, N-methyl methacrylamide, N-ethyl methacrylamide, N-dodecyl methacrylamide, N,N-dimethylaminoethyl acrylamide, quaternized N,N-dimethylaminoethyl acrylamide, N,N-dimethylaminoethyl methacrylamide, quaternized N,N-dimethylaminoethyl methacrylamide, N,N-dimethylaminoethyl acrylate, N,N-dimethylaminoethyl methacrylate, quaternized N,N-dimethyl-aminoethyl acrylate, quaternized N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, maleic anhydride and its half esters, fumaric acid, itaconic acid, itaconic anhydride and its half esters, crotonic acid, angelic acid, diallyldimethyl ammonium chloride, vinyl pyrrolidone, vinyl imidazole, methyl vinyl ether, methyl vinyl ketone, maleimide, vinyl pyridine, vinyl furan, styrene sulphonate, allyl alcohol, allyl citrate, allyl tartrate, vinyl acetate, vinyl alcohol, vinyl caprolactam and mixtures thereof.

Particularly preferred monomers are the mono-esters derived from acrylic or methacrylic acid and a glycol, in particular ethylene glycol and especially its acrylic acid mono-ester (i.e. 2-hydroxyethyl acrylate). Such monomers lend themselves easily to the addition of at least one side chain which is formed from a hair fibre targeting group. In particular, they may be used in the manufacture of hair substantive polymers comprising a polymeric backbone bearing at least one side chain comprising a catechol group, said side chain being covalently linked to the polymeric backbone.

Monomers useful in forming the polymeric backbone also include polymerisable organosiloxane monomers.

Accordingly, the polymeric backbone may suitable include a chain of monomeric units of formula —SiR₂—O—, in which each R group is independently selected from monovalent, optionally substituted, linear or branched $C_{1-18}$ hydrocarbon radicals.

Examples of monovalent, unsubstituted radicals are alkyl radicals, such as the methyl, ethyl, n-propyl, iso-propyl, n-butyl, iso-butyl, tert-butyl, n-pentyl, iso-pentyl, neo-pentyl and tert-pentyl radical; alkoxy radicals, such as the methoxy, ethoxy, n-propoxy, iso-propoxy, n-butoxy, iso-butoxy, tert-butoxy, n-pentoxy, iso-pentoxy, neo-pentoxy and tert-pentoxy radical; hexyl radicals, such as the n-hexyl radical; alkenyl radicals, such as the vinyl, allyl, 5-hexenyl, 4-vinylcyclohexyl and the 3-norbornenyl radical; cycloalkyl radicals, such as cyclopentyl, cyclohexyl, 4-ethylcyclohexyl and cycloheptyl radical; norbornyl radicals and methylcyclohexyl radicals; aryl radicals, such as the phenyl, biphenylyl, napthyl, anthryl and phenanthryl radical; alkaryl radicals, such as o-, m- and p-tolyl radical, xylyl radicals and ethylphenyl radical; and aralkyl radicals, such as the benzyl, styryl, and phenylethyl radicals.

Examples of monovalent, substituted radicals are halogenated hydrocarbon radicals, such as the chloromethyl, 3-chloropropyl, 3-bromopropyl, 3,3,3-trifluoropropyl and 5,5,5,4,4,3,3-heptafluoropentyl radical and the chlorophenyl, dichlorophenyl and trifluorotolyl radical; mercaptoalkyl radicals, such as the 2-mercaptoethyl and 3-mercaptopropyl radical; cyanoalkyl radicals, such as the 2-cyanoethyl and 3-cyanopropyl radical; aminoalkyl radicals, such as the 3-aminopropyl, N-(2-aminoethyl)-3-aminopropyl and N-(2-aminoethyl)-3-amino-(2-methyl)propyl radical; aminoaryl radicals, such as the aminophenyl radical; acyloxyalkyl radicals, such as the 3-acryloxypropyl and 3-methacryloxypropyl radical; and hydroxyalkyl radicals, such as the hydroxypropyl radical.

Preferred monovalent radicals are independently selected from unsubstituted or substituted $C_1$ to $C_6$ alkyl radicals or the phenyl radical, in particular the methyl, ethyl, propyl or phenyl radical.

Mixtures of any of the above described monomers may be used to form the polymeric backbone.

The polymeric backbone could also be formed from or derived from naturally occurring polymeric materials such as proteins, polysaccharides, cellulosics and modified cellulosics, starch and modified starches, xanthan gums, and guar gums.

Side Chain (a)

The hair substantive polymer of the invention comprises at least one side chain (a) which is formed from a hair fibre targeting group which is covalently linked to the polymeric backbone.

The hair fibre targeting group is a non-cationic species which is capable of specifically interacting with the protein surface of the hair fibre in a non-covalent interaction having a bond energy ranging from 0.5 to 3 Kcal/mol, when the composition is applied to hair.

Examples of suitable non-covalent interactions include van-der-Waals, pi-stacking, and hydrogen bonding interactions.

The hair fibre targeting group is a group which is capable of specifically interacting with the protein surface of the hair fibre in a hydrogen bonding interaction having a bond energy ranging from 1 to 3 Kcal/mol, when the composition is applied to hair.

Suitable hair fibre targeting groups include free amino groups and free phenolic hydroxyl groups.

Illustrative materials which may be linked to the polymeric backbone to introduce free amino groups include alkyl amines (e.g., 1,3-diaminopropane, 1,6-hexanediamine, ethylene diamine, diethylenetriamine), unsaturated hydrocarbon amines (e.g., allylamine), hydroxy amines (e.g., ethanolamine, hydroxyamine), amidines (e.g., melamine), imines (e.g., polyethyleneimine), amino acids (e.g., tryptophan), polyamines, polyamides, alkaloids and mixtures thereof.

A preferred example is the amino acid tryptophan. This can provide superior bonding strength to the protein surface of the hair fibre.

Illustrative materials which may be linked to the polymeric backbone to introduce free phenolic hydroxyl groups include dopamine (i.e., 3,4-dihydroxyphenylethylamine hydrochloride), tyramine (4-hydroxyphenylethylamine hydrochloride), DOPA (3,4-dihydroxyphenyl-L-alanine), 2-aminophenol, 3-aminophenol, 4-aminophenol, caffeic acid, catechol, 4-methylcatechol, 4-aminocatechol, 4-hydroxycinnamic acid, 4-hydroxy-3-methoxycinnamic acid, 4-hydroxy-3,5-dimethoxy-cinnamic acid, tannin, flavonoids, lignin and poly(4-vinylphenol).

Preferred examples are phenolic groups which include two phenolic hydroxyl groups in an ortho position relative to each other on the aromatic ring (i.e. a catechol group). Particularly preferred examples are phenolic groups which include two phenolic hydroxyl groups in the 3,4-position on the aromatic ring. This can provide superior bonding strength to the protein surface of the hair fibre.

Mixtures of any of the above described materials may be used to introduce hair fibre targeting groups to the polymeric backbone.

In order to optimise the interaction between the hair fibre targeting group and the protein surface of the hair fibre, it may in certain circumstances be advantageous to introduce a flexible spacer between the polymeric backbone and the hair fibre targeting group. This is because steric hindrance may inhibit the interaction between the hair fibre targeting group and the protein surface of the hair fibre, if the hair fibre targeting group lies in too close proximity to the polymer backbone.

Suitable flexible spacers may be selected from the following divalent organic groups:

—$R^1$—C(O)—O—;

—$R^1$—O—C(O)—O—;

—$R^1$—C(O)—N($R^2$)—;

—$R^1$—O—C(O)—N($R^2$)—, or

—$R^1$—N($R^2$)—C(O)—N($R^3$)—;

in which $R^1$ is a divalent, optionally substituted, linear or branched $C_1$-$C_{18}$ hydrocarbon radical, and $R^2$ and $R^3$ are independently selected from monovalent, optionally substituted, linear or branched $C_{1-18}$ hydrocarbon radicals.

Examples of monovalent, unsubstituted radicals are alkyl radicals, such as the methyl, ethyl, n-propyl, iso-propyl, n-butyl, iso-butyl, tert-butyl, n-pentyl, iso-pentyl, neo-pentyl and tert-pentyl radical; alkoxy radicals, such as the methoxy, ethoxy, n-propoxy, iso-propoxy, n-butoxy, iso-butoxy, tert-butoxy, n-pentoxy, iso-pentoxy, neo-pentoxy and tert-pentoxy radical; hexyl radicals, such as the n-hexyl radical; alkenyl radicals, such as the vinyl, allyl, 5-hexenyl, 4-vinylcyclohexyl and the 3-norbornenyl radical; cycloalkyl radicals, such as cyclopentyl, cyclohexyl, 4-ethylcyclohexyl and cycloheptyl radical; norbornyl radicals and methylcyclohexyl radicals; aryl radicals, such as the phenyl, biphenylyl, napthyl, anthryl and phenanthryl radical; alkaryl radicals, such as o-, m- and p-tolyl radical, xylyl radicals and ethylphenyl radical; and aralkyl radicals, such as the benzyl, styryl, and phenylethyl radicals.

Examples of monovalent, substituted radicals are halogenated hydrocarbon radicals, such as the chloromethyl, 3-chloropropyl, 3-bromopropyl, 3,3,3-trifluoropropyl and 5,5,5,4,4,3,3-heptafluoropentyl radical and the chlorophenyl, dichlorophenyl and trifluorotolyl radical; mercaptoalkyl radicals, such as the 2-mercaptoethyl and 3-mercaptopropyl radical; cyanoalkyl radicals, such as the 2-cyanoethyl and 3-cyanopropyl radical; aminoalkyl radicals, such as the 3-aminopropyl, N-(2-aminoethyl)-3-aminopropyl and N-(2-aminoethyl)-3-amino-(2-methyl)propyl radical; aminoaryl radicals, such as the aminophenyl radical; acyloxyalkyl radicals, such as the 3-acryloxypropyl and 3-methacryloxypropyl radical; and hydroxyalkyl radicals, such as the hydroxypropyl radical.

Preferred monovalent radicals are independently selected from unsubstituted or substituted $C_1$ to $C_6$ alkyl radicals or the phenyl radical, in particular the methyl, ethyl, propyl or phenyl radical.

Examples of divalent hydrocarbon radicals are linear or branched saturated alkylene radicals, such as the methylene and ethylene radical, as well as propylene, butylene, pentylene, hexylene, cyclohexylene and octadecylene radicals; alkoxyalkylene radicals such as the methoxyethylene and ethoxyethylene radical; unsaturated alkylene or arylene radicals, such as the hexenylene radical and phenylene radicals; alkarylene radicals such as the methylphenylene and ethylphenylene radical, and alkoxyarylene radicals such as the methoxyphenylene and ethoxyphenylene radical. The divalent hydrocarbon radical $R^1$ can be interrupted by divalent radicals, bonded to carbon atoms on both sides, such as —O—, —C(O)O—, —O(O)C—, —CONR$^4$—, —NR$^4$C(O)— and —C(O)—, where $R^4$ is hydrogen or a monovalent, optionally substituted, linear or branched $C_{1-18}$ hydrocarbon radical as described above.

Preferred divalent radicals are alkylene radicals, preferably covalently linked to both the polymer backbone and hair fibre targeting group by ester functionality.

Preferred hair substantive polymers comprise both a flexible spacer between the polymeric backbone and the hair fibre targeting group and a hair fibre targeting group that is a catechol group. It is particularly preferred that the ortho hydroxyls of the catechol group are in the 3,4-positions relatively to the attachment of the catechol group to the flexible spacer.

Particularly preferred hair substantive polymers are partial esters of poly(hydroxyethylacrylate) and poly(hydroxyethylmethacrylate) with 3,4-dihydroxybenzoic acid. Especially preferred hair substantive polymers are partial esters of poly(hydroxyethylacrylate) with 3,4-hydroxybenzoic acid. In such hydroxyethylacrylate and hydroxyethylmethacrylaye polymers, the degree of esterification with 3,4-hydroxybenzoic acid is preferably from 1 to 50, more preferably from 5 to 35, and most preferably from 10 to 20 mole %. The molecular weight of such polymers is preferably from 1,000 to 1,000,000, more preferably from 1,000 to 500,000, and most preferably from 10,000 to 100,000.

Side Chain (b)

In some embodiments, it is preferred that the hair substantive polymer includes at least one side chain which is different to side chain (a) and which comprises a hair benefit agent.

Examples of typical hair benefit agents include hair conditioning agents, (such as humectants, softeners and cuticle lubricants), hair colouring agents, antimicrobial compounds, UV-absorbing compounds, fluorescers, hair strengthening agents (such as fibre repair agents or fibre rebuilding agents), antioxidants, perfumes, and mixtures thereof.

A flexible spacer such as described above may also be introduced between the polymeric backbone and the material which is linked to the polymeric backbone to introduce the hair benefit agent.

Manufacture

The hair substantive polymer may be manufactured using polymerisation techniques known to those skilled in the art.

In one suitable technique, a preformed polymer backbone may be chemically modified by the introduction of reactive groups, thus enabling linkage of the backbone to side chains (a) and optionally (b) as described above. The choice of reactive groups may be selected by the skilled worker according to the chemistry of the modification reaction. Examples of reactive groups are allylic, alpha-olefin, acid, anhydride, amine and isocyanate groups.

Alternatively, the hair substantive polymer may be constructed by direct reaction of polymerisable monomeric "building blocks", at least some of which comprise the groups of side chains (a) and optionally (b) as described above.

WO03/008376 describes a route for the conjugation of DOPA moieties to polymeric systems such as poly(ethylene glycol) or poly (alkylene oxide).

The synthesis of a 3,4-dihydroxystyrene containing polymer by polymerisation of aromatic vinyl monomers using a radical polymerisation technique is described by Yang et al., *Macromol. Rapid Commun.* 19, 241-246 (1998).

Compositions

The total amount of hair substantive polymer in hair treatment compositions of the invention generally ranges from 0.1 to 5%, preferably from 0.15 to 3%, more preferably from 0.2 to 2% by total weight hair substantive polymer based on the total weight of the composition.

Hair treatment compositions according to the invention may suitably take the form of shampoos, conditioners, sprays, mousses, oils, styling products, including leave on products, hair colouring products or lotions.

Compositions in accordance with the invention are preferably formulated as products for the treatment of hair and subsequent rinsing.

A component that is present in all compositions according to the invention is a cosmetically acceptable carrier material, such as water, typically at a level of from 50 to 90% by weight of the composition.

A perfume or fragrance is a component that is preferably present in all compositions according to the invention, typically at a level of from 0.1 to 5% by weight of the composition.

Shampoo Compositions

A particularly preferred hair treatment composition in accordance with the invention is a shampoo composition.

Such a shampoo composition will comprise one or more cleansing surfactants which are cosmetically acceptable and suitable for topical application to the hair. Further surfactants may be present as emulsifiers.

Suitable cleansing surfactants are selected from anionic, amphoteric and zwitterionic surfactants, and mixtures thereof.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, alkyl ester carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl sulpho succinate, ammonium lauryl sulphosuccinate, ammonium lauryl sulphate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n is from 1 to 3), ammonium lauryl sulphate and ammonium lauryl ether sulphate(n) EO, (where n is from 1 to 3).

The total weight of anionic cleansing surfactant in shampoo compositions of the invention is generally from 5 to 30, preferably from 6 to 20, more preferably from 8 to 16 percent by weight of the composition.

Co-surfactant

The shampoo composition can optionally include co-surfactants, preferably an amphoteric or zwitterionic surfactant, which can be included in an amount ranging from 0 to about 8, preferably from 1 to 4 percent by weight of the composition.

Examples of amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred co-surfactant is a nonionic surfactant, which can be included in an amount ranging from 0 to 8, preferably from 2 to 5 percent, by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain $C_5$ to $C_{20}$ alkyl or alkenyl group, G is a saccharide group and n is from 1 to 10.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The shampoo composition can also optionally include one or more cationic co-surfactants included in an amount ranging from 0.01 to 10, more preferably from 0.05 to 5, most preferably from 0.05 to 2 percent by weight of the composition. Useful cationic surfactants are described hereinbelow in relation to conditioner compositions.

The total weight of surfactant (including any co-surfactant, and/or any emulsifier) in shampoo compositions of the invention is generally from 5 to 50, preferably from 5 to 30, more preferably from 10 to 25 percent by weight of the composition.

Cationic Polymer

The shampoo composition can optionally include cationic polymer(s). Suitable cationic polymers for use in shampoo compositions of the invention are the same as those described above.

The cationic polymer will generally be present in compositions of the invention at levels of from 0.01 to 5, preferably from 0.05 to 1, more preferably from 0.08 to 0.5 percent by weight of the composition.

Conditioner Compositions

Another preferred form of hair treatment composition in accordance with the invention is a conditioner for the treatment of hair (typically after shampooing) and subsequent rinsing.

Conditioning Surfactant

Conditioner compositions usually comprise one or more conditioning surfactants which are cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

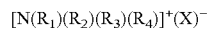

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C16 to C22.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. Particularly useful quaternary ammonium cationic surfactants for use in hair conditioners of the invention are cetyltrimethylammonium chloride, available commercially, for example as GENAMIN CTAC, ex Hoechst Celanese and Arquad 16/29 supplied by Akzo Nobel, and behenyltrimethylammonium chloride (BTAC) such as Genamin KDM-P supplied by Clariant. These may be the same as but are in addition to and separate from any quaternary ammonium compounds that may be used as charged organic molecule.

Further suitable cationic systems are primary, secondary, and tertiary fatty amines used in combination with an acid to provide the cationic species. These are the same as but are in addition to and separate from any such amines and acids that may be used as charged organic molecule. The alkyl groups of such amines preferably have from 12 to 22 carbon atoms, and can be substituted or unsubstituted.

Particularly useful are amido substituted tertiary fatty amines, in particular tertiary amines having one $C_{12}$ to $C_{22}$ alkyl or alkenyl chain. Such amines, useful herein, include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

As stated previously, these amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to $H^-$ from the acid is preferably from about 1:0.3 to 1:1.2, and more preferably from about 1:0.5 to about 1:1.1.

In the conditioners of the invention, the level of cationic surfactant is preferably from 0.01 to 10, more preferably 0.05 to 5, most preferably 0.1 to 2 percent by weight of the total composition.

Fatty Materials

Conditioner compositions of the invention preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Other Components

In a preferred embodiment, the hair treatment composition, especially if it is a shampoo composition, further comprises from 0.1 to 5 percent of a suspending agent, by weight of the total composition. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Compositions in General

Compositions of this invention may contain any other ingredient normally used in hair treatment formulations, including further silicone or non-silicone hair conditioning oils. These other ingredients may include viscosity modifiers, preservatives, colouring agents, polyols such as glycerine and polypropylene glycol, chelating agents such as EDTA, antioxidants, fragrances, antimicrobials and sunscreens. Each of these ingredients will be present in an amount effective to accomplish its purpose. Generally these optional ingredients are included individually at a level of up to 5% by weight of the total composition.

EXAMPLES

Uptake and Substantivity of Dihydroxybenzene Isomers on Human Hair

Experiments have been carried out to investigate the uptake and substantivity of the three isomers of dihydroxybenzene on human hair. The experimental method was as follows:

Glass columns were packed with a known mass of hair from a common source. Solutions of each of the three isomers of dihydroxybenzene were accurately prepared using a known mass of dihydroxybenzene and an ethanol/water mixture as solvent. A solvent blank (containing no dihydroxybenzene) was included in the experimental matrix. A known volume of solution was then pipetted into a packed column of hair and the eluent collected in a clean vial of known weight which was then firmly capped and placed on one side. A known volume of ethanol was then pipetted into the column to rinse the hair and the eluent was again collected in a clean vial of known weight. This process was repeated twice and the collection vial was capped and retained.

Uptake calculations: the vial containing the eluent from the initial introduction of dihydroxybenzene was uncapped and the solvent removed by evaporation under nitrogen. The dry weight of the vial was measured, allowing a calculation of the weight of solute collected in the vial. The weight of solute collected in the control vial (the vial used to collect the eluent from the solvent blank) was subtracted from all the data, giving the weight of dihydroxybenzene eluted from each column. This was subtracted from the known weight of dihydroxybenzene present in the initial solution, allowing a calculation of the weight of dihydroxybenzene retained on the hair after the initial elution. This is expressed as a percentage in the 'Uptake' column in the table below.

Substantivity calculations: The vial containing the eluent from the 3× ethanol/water (50:50 mixture) rinse was uncapped and the solvent removed by evaporation under nitrogen. The dry weight of the vial was measured, allowing a calculation of the weight of solute collected in the vial. The weight of solute collected in the control vial (the vial used to collect the eluent from the solvent blank) was subtracted from all the data, giving the weight of dihydroxybenzene eluted from each column during the rinse. This was subtracted from the known weight of dihydroxybenzene present in the initial solution less the amount known to have been eluted directly from the column, allowing a calculation of the weight of dihydroxybenzene retained on the hair after the rinse. This is expressed as a percentage in the 'Substantivity' column in Table 1 below.

TABLE 1

| Dihydroxybenzene isomer | Uptake on hair (%) | Substantivity on hair (%) |
|---|---|---|
| 1,2 dihydroxybenzene (Catechol) | 91 | 88 |
| 1,3 dihydroxybenzene (Resorcinol) | 30 | 17 |
| 1,4 dihydroxybenzene (Hydroquinone) | 33 | 7 |

The data clearly show that catechol is much more substantive to human hair than either of its isomers. This is especially true for substantivity, which was measured after rinsing.

Preparation of Poly(2-hydroxyethyl acrylate) (PHEA)

Materials:

2-hydroxyethyl acrylate (HEA) (96%, ex TCI) was purified by extraction with n-hexane 10 times (to remove di-acrylate impurity). The hexane was then removed by rotary evaporation.

DMF (AR grade) was distilled in vacuo after stirring with calcium hydroxide overnight.

AIBN was purified by re-crystallization.

3-mercapto-1,2-propanediol (MP) (ex Aldrich) was introduced as a chain transfer agent and used as received.

1,3-dicyclohexylcarbodiimide (DCC) was also used as received.

Polymerisation:

HEA (20 ml), AIBN (4.506 g), and MP (3.26 g) were dissolved in anhydrous DMF (80 ml) in a 250 ml three-necked flask. The polymerisation was performed at 70° C.

under a nitrogen atmosphere for 8 hours. The resulting PHEA was precipitated by the addition of ether (200 ml) and twice purified by re-precipitation from methanol into ether.

The molecular weight of the PHEA was determined to be 11,800 by GPC (using an Agilent 1100 Series GPC system).

Preparation of PHEA with Side Chains Bearing Catechol Groups (Polymer 1)

PHEA (3.2 g, as prepared above) and 3,4-dihydroxybenzoic acid (1.27 g) were dissolved in DMF (15 ml) in a 100 ml flask. This solution was cooled to 0° C. and a solution of DCC (1.706 g) in DMF (5 ml) was added dropwise, with stirring, over a period of 10 minutes. The reaction mixture was allowed to warm to room temperature and was stirred for a further 48 hours. After this time, the solution was filtered to remove the dicyclohexylurea by-product and the resulting clear solution was poured in 200 ml ether to precipitate the crude product. The crude product was twice purified by re-precipitation from methanol into ether. The purified product (Polymer 1) was determined to have a degree of catechol-substitution of 14 mole % by $^1$H NMR (using a Bruker 400 instrument).

Substantivity of PHEA and Polymer 1 on Human Hair

The substantivity of PHEA and Polymer 1 (both as prepared above) on human hair was measured. The polymer samples were each dissolved in water to give solutions of 1% w/w concentration. 1 ml of each solution was dosed through a column containing approximately 0.35 g of hair. The test method was essentially the same as that used to measure the substantivity of the dihydroxybenzene isomers, as described above, and the substantivity of the polymer samples was calculated in the same manner.

It was found that the PHEA sample had a substantivity of 4.1%, whereas Polymer 1 had a substantivity of 15.1%. This result clearly shows that Polymer 1 is much more substantive to human hair than the control polymer lacking catechol substitution.

Formulation Examples

The shampoo compositions shown in Table 2 may be prepared by methods known in the art. Composition 1 is a cleansing shampoo and Composition 2 is a cleansing and conditioning shampoo. Percentages are by weight.

TABLE 2

Shampoo Compositions

|  | Composition 1 | Composition 2 |
| --- | --- | --- |
| Sodium laureth sulphate | 12% | 12% |
| Cocoamidopropyl betaine | 1.5% | 1.5% |
| Jaguar C13S (Guar hydroxypropyltrimonium chloride) | — | 0.2% |
| Fragrance | 0.5% | 0.5% |
| Dimethicone | — | 2% |
| Carbopol 980 (Carbomer) | — | 0.4% |
| Timiron MP-1001 (Mica) | — | 0.2% |
| Sodium Chloride | 1.5% | 0.75% |
| SoftCat SKMH (Polyquaternium-67) | 0.2% | — |
| DMDM Hydantoin | 0.2% | 0.2% |
| Polymer 1 | 0.25% | 0.25% |
| Water (Aqua) | to 100% | to 100% |

The hair conditioning compositions shown in Table 3 may be prepared by methods known in the art. Composition 3 is a conditioner and Composition 4 is a leave on product. Percentages are by weight.

TABLE 3

Conditioning Compositions

|  | Composition 3 | Composition 4 |
| --- | --- | --- |
| Cetearyl alcohol | 3% | 3% |
| Cetyltrimethylammonium chloride | 0.7% | 0.7% |
| Natrosol 250HHR (Hydroxyethyl cellulose) | 0.15% | — |
| Fragrance | 0.4% | 0.3% |
| Dimethicone | 3% | 1% |
| Luviquat FC550 (Polyquaternium-16) | — | 1.5% |
| Polysurf-67 (Cetyl hydroxyethyl cellulose) | — | 0.02% |
| DMDM Hydantoin | 0.2% | 0.2% |
| Polymer 1 | 0.5% | 1% |
| Water (Aqua) | to 100% | to 100% |

The invention claimed is:

1. A hair treatment shampoo composition comprising:
   a) 8 to 16% by wt. of an anionic surfactant selected from the group consisting of sodium lauryl sulphate, sodium lauryl ether sulphate, ammonium lauryl sulphate and ammonium lauryl ether sulphate;
   b) 1 to 4% by wt. of an amphoteric or zwitterionic cosurfactant;
   c) 50 to 90% water; and
   d) 0.1 to 5% by wt. of a hair substantive polymer, the hair substantive polymer comprising a polymeric backbone bearing:
      (i) at least one side chain which is formed from a hair fibre targeting group which is covalently linked to the polymeric backbone, the hair fibre targeting group being a non-cationic species which is capable of specifically interacting with the protein surface of the hair fibre in a non-covalent interaction having a bond energy ranging from 0.5 to 3 Kcal/mol, when the composition is applied to hair; wherein the hair fibre targeting group comprises a partial ester of poly(hydroxyethylacrylate) with 3,4-dihydroxybenzoic acid, a partial ester of poly(hydroxyethylmethacrylate) with 3,4-dihydroxybenzoic acid or mixtures thereof;
      (ii) optionally, at least one side chain different from side chain (i) and which different side chain comprises a hair benefit agent.

2. A hair treatment composition according to claim 1, in which the hair benefit agent is selected from hair conditioning agents, hair colouring agents, antimicrobial compounds, UV-absorbing compounds, fluorescers, hair strengthening agents, antioxidants, perfumes, and mixtures thereof.

3. A method of enhancing the substantivity of a molecule to hair to provide more efficient deposition and delivery of benefit agent to the hair which method comprises applying to the hair a composition according to claim 1.

4. A hair treatment shampoo composition according to claim 1, wherein said substantive polymer comprises a flexible spacer between the polymeric backbone and the catechol group on said dihydroxybenzoic acid.

5. A hair treatment shampoo composition according to claim 1, wherein the degree of esterification with 3,4-dihydroxybenzoic acid is from 5 to 35 mole %.

6. A hair treatment shampoo composition according to claim 1, wherein the molecular weight of hair substantive polymer is from 1,000 to 500,000.

7. A hair treatment shampoo composition according to claim 1 further comprising a perfume or fragrance.

8. A hair treatment conditioner composition comprising:
a) 0.05-5% by wt. of a cationic conditioning surfactant corresponding to general formula:

$[N(R1)(R2)(R3)(R4)]^+(X)^-$ in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion selected from halogen, acetate, citrate, lactate, glycolate, phosphate, nitrate, sulphate, and alkylsulphate radicals;
b) 0.1 to 10% by wt. of fatty material which is fatty alcohol, alkoxylated fatty alcohol, fatty acid or mixtures thereof, the ratio of cationic surfactant to fatty alcohol being 10:1 to 1:10; and
c) 0.1 to 5% by wt. of a hair substantive polymer, the hair substantive polymer comprising a polymeric backbone bearing:
   (i) at least one side chain which is formed from a hair fibre targeting group which is covalently linked to the polymeric backbone, said hair fibre targeting group being a non-cationic species which is capable of specifically interacting with the protein surface of the hair fibre in a non-covalent interaction having a bond energy ranging from 0.5 to 3 Kcal/mol, when the composition is applied to hair; wherein said targeting group comprises a partial ester of poly(hydroxyethylacrylate) with 3,4-dihydroxybenzoic acid, a partial ester of poly(hydroxyethylmethacrylate) with 3,4-dihydroxybenzoic acid or mixtures thereof;
   (ii) optionally, at least one side chain different from side chain (i) and which different side chain comprises a hair benefit agent.

* * * * *